United States Patent

Kurishita et al.

[11] Patent Number: 5,144,249
[45] Date of Patent: Sep. 1, 1992

[54] OXYGEN SENSOR

[75] Inventors: Akiyoshi Kurishita, Kasugai; Masanori Katsu, Nagoya; Masami Kato, Handa, all of Japan

[73] Assignee: NGK Insulators, Ltd., Nagoya, Japan

[21] Appl. No.: 668,552

[22] Filed: Mar. 13, 1991

[30] Foreign Application Priority Data

Mar. 22, 1990 [JP] Japan .................................. 2-72693

[51] Int. Cl.$^5$ .............................. G01N 27/58
[52] U.S. Cl. ................................ 324/439; 204/426; 204/429
[58] Field of Search ................. 324/439, 450, 446; 204/426, 428, 429

[56] References Cited

U.S. PATENT DOCUMENTS

| 4,126,532 | 11/1978 | Takao et al. | 204/426 |
|---|---|---|---|
| 4,145,272 | 3/1979 | Nakamura et al. | 204/428 |
| 4,282,080 | 8/1981 | Müller et al. | |
| 4,294,679 | 10/1981 | Maurer et al. | |
| 4,416,763 | 11/1983 | Fujishiro | 204/426 |
| 4,450,065 | 5/1984 | Yamada et al. | |
| 4,464,244 | 8/1984 | Uchida | 204/429 |
| 4,502,939 | 3/1985 | Holfelder et al. | |
| 4,642,174 | 2/1987 | Shibata | 204/428 |
| 4,732,663 | 3/1988 | Kato et al. | |
| 4,851,105 | 7/1989 | Ishiguro et al. | 204/429 |

FOREIGN PATENT DOCUMENTS 128348 7/1985 Japan .

*Primary Examiner*—Kenneth A. Wieder
*Assistant Examiner*—Maura K. Regan
*Attorney, Agent, or Firm*—Armstrong & Kubovcik

[57] ABSTRACT

An oxygen sensor has an oxygen sensor element in the form of an elongated plate having an oxygen detection section at the end of said oxygen sensor element. The oxygen detection section generates electromotive force between electrodes according to oxygen concentration or varies electrical resistance. Chamfering is applied to ridges formed parallel to the lengthwise direction of the oxygen sensor element which is exposed to gas to be measured. According to this sensor, cracks do not occur. Therefore, oxygen concentration detecting function is not damaged even when the oxygen sensor element is thermally stressed.

4 Claims, 5 Drawing Sheets

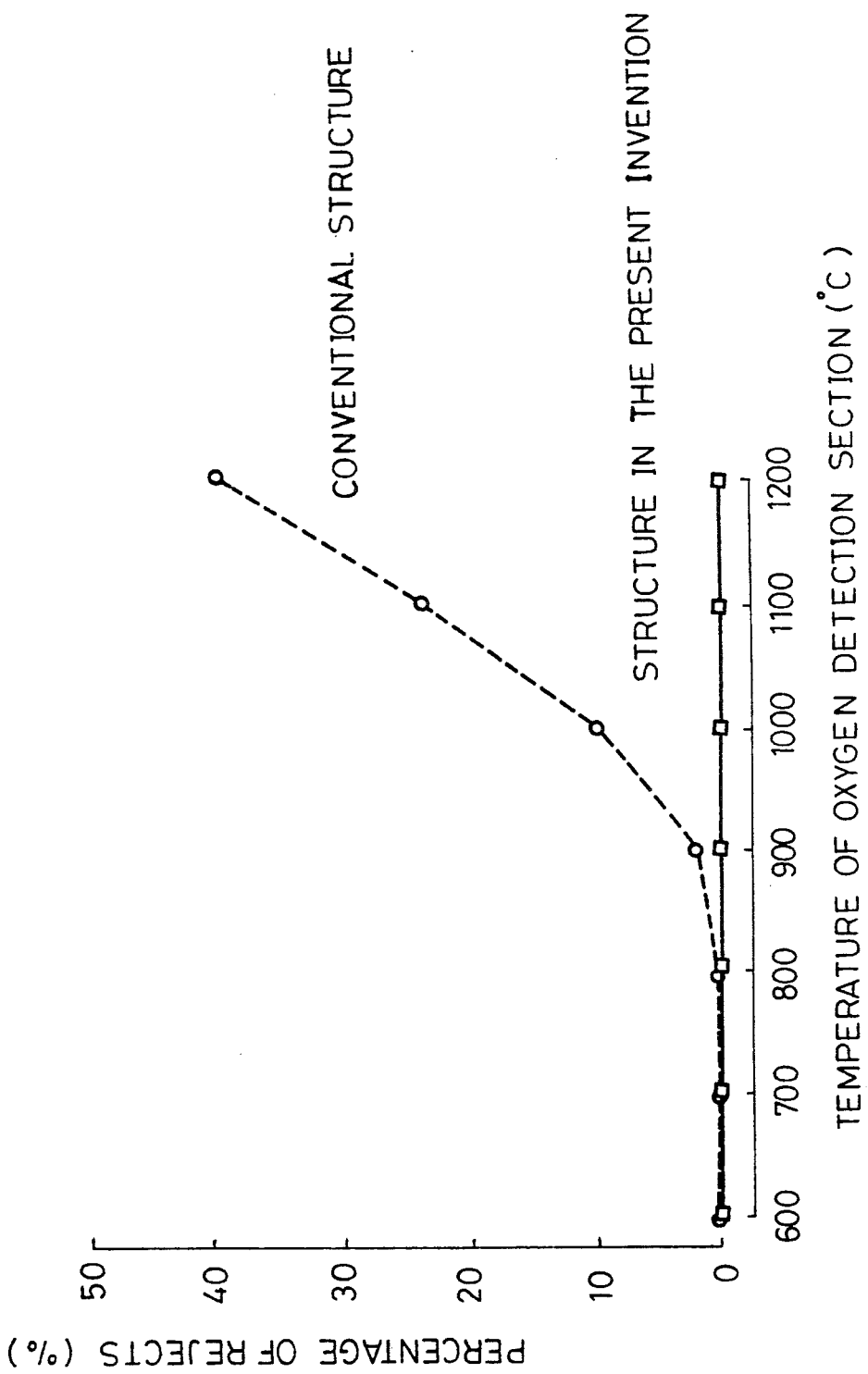

OXYGEN SENSOR

BACKGROUND OF THE INVENTION

1. Field of the Invention

The present invention relates to an oxygen sensor and, more particularly to an improvement of a plate oxygen sensor element which is used to detect the concentration of oxygen in gas, particularly in the gas exhausted from an internal combustion engine.

2. Description of the Prior Art

There have been known oxygen sensors employed as an oxygen concentration detector. These oxygen sensors perform purification of exhausted gas and economization on fuel consumption and the like by detecting the oxygen concentration in exhausted gas from an internal-combustion engine, and by suitably controlling combustion conditions of the internal-combustion engine based on the detection signals regarding the oxygen concentration.

One of these sensors employs a sensor element comprising a partition of a solid electrolyte having oxygen ion conductivity, such as zirconium oxide doped with calcium oxide, yttrium oxide or the like, the both surfaces of the partition being provided with respective electrodes. One of the electrodes is exposed to reference atmosphere and the other is exposed to gas to be measured, such as exhaust gas and the like. With this arrangement, electromotive force obtained through applying the theory of oxygen concentration cell is employed as the detection signal.

Among such oxygen detecting elements, nowadays there has been noted an elongated plate detecting element instead of a cylindrical detecting element with a bottom attached, for ease of fabrication, volume reduction and the like, either end of the plate being provided with an oxygen detection section to be exposed to gas to be measured, such as exhaust gas and the like. Japanese Patent Laid-Open Nos. 58-153155 and 61-97562 show examples of such plate oxygen detecting elements.

There has been known another type of an oxygen sensor employing a sensor element in which an elongated plate substrate is provided with an oxide at the surface, the oxide varying electrical resistance depending upon oxygen concentration, such as titanium oxide. With this arrangement, the sensor element is exposed to gas to be measured, such as exhaust gas and the like, in order to detect the variation of electrical resistance caused by partial pressure of oxygen.

FIG. 4 illustrates an example of such plate oxygen sensor element.

Such oxygen sensor element 12, as illustrated in FIG. 4, has an oxygen detection section 5 which is exposed to gas to be measured, such as exhaust gas having generally high temperature. In order that the oxygen detecting capacity of the oxygen detection section 5 in such oxygen sensor element 12 may sufficiently function, in some cases, the oxygen detection section 5 is maintained at a high temperature by a heater built in the oxygen sensor element 12. Consequently, the oxygen sensor element 12 may undergo thermal stress.

This oxygen sensor element 12 is, however, in the form of a plate; therefore, there arises stress concentration at the respective ridges 6 thereof so that cracks occur and the oxygen concentration detecting function by the sensor element 12 is damaged.

SUMMARY OF THE INVENTION

Accordingly, an object of the present invention is to solve the foregoing problems.

According to the present invention, there is provided an oxygen sensor comprising an oxygen sensor element in the form of an elongated plate having an oxygen detection section at the end of said oxygen sensor element, the oxygen detection section generating electromotive force between electrodes according to oxygen concentration or varying electrical resistance, chamfering being applied to ridges formed parallel to the lengthwise direction of the oxygen sensor element which is exposed to gas to be measured. The said oxygen detection section generating electromotive force comprises a measuring electrode formed on one surface of solid electrolytic body, a porous protective layer, and a reference electrode formed on the other surface of the solid electrolytic body.

BRIEF DESCRIPTION OF THE DRAWINGS

FIG. 2 is a graph showing the rate of crack initiation by thermal shock test;

DESCRIPTION OF THE PREFERRED EMBODIMENTS

The present invention will now be described by way of the following examples which are provided for illustrative purposes and should not be construed as limiting the invention.

Figure 1A:
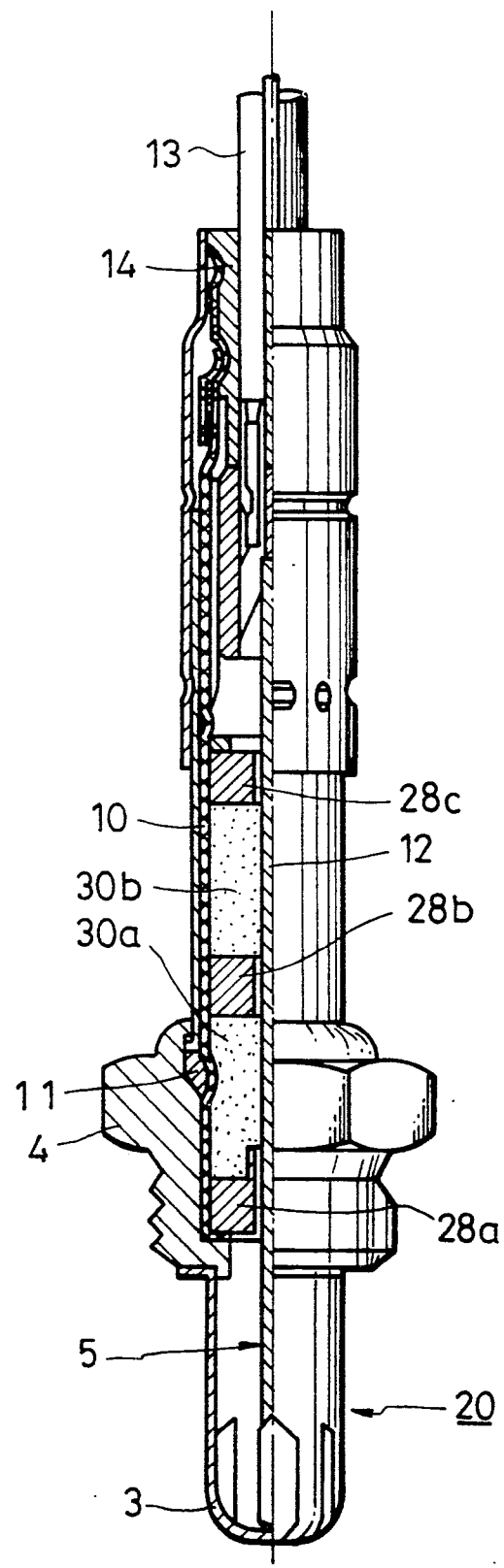
FIG. 1(a) is a cross-sectional view illustrating an oxygen sensor in the present invention.

In FIGS. 1(a), (b), (c) and (d), numeral 12 denotes an oxygen sensor element in the form of an elongated plate which is formed of solid electrolyte mainly composed of zirconia. As has been known, the oxygen sensor element 12 has an oxygen detection section 5 at the end thereof. Specifically, as disclosed in Japanese Patent Laid-Open No. 60-128348 previously filed by applicant, the oxygen detection section 5, as illustrated in FIG. 1(c), comprises: a measuring electrode 40 which is formed on the outer surface of solid electrolytic body 1 mainly composed of zirconia and having oxygen ion conductivity, and is in contact with outer gas to be measured; a porous protective layer 2 which covers the entire surface of the electrode 40; a reference electrode 41 which is formed on the inner surface of the solid electrolytic body 1 and is in contact with reference gas such as air; and heater elements 43 integrally formed in the solid electrolytic body by printing and laminating for heating the oxygen detection section 5 to the predetermined temperature.

Figure 1B:
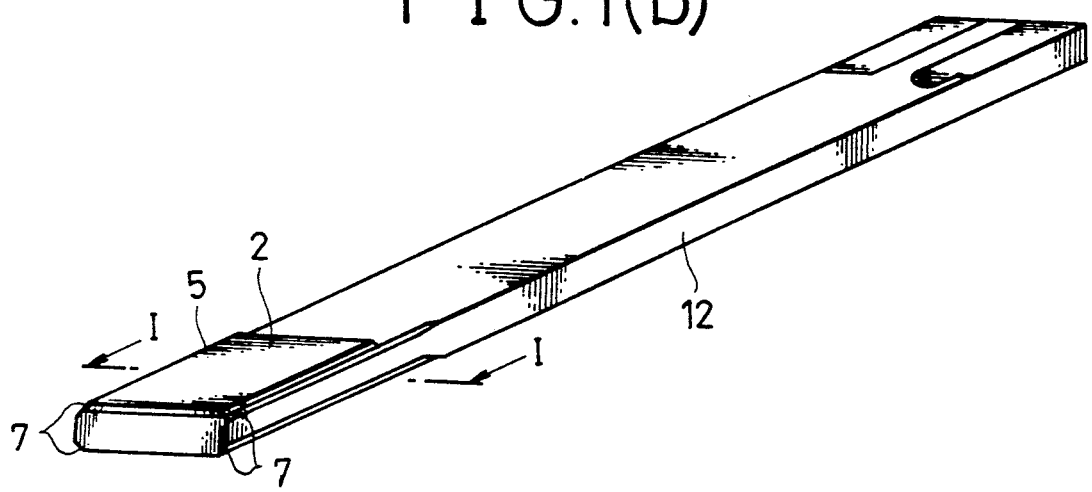
FIG. 1(b) is a perspective view of an example of an oxygen sensor element employed in the oxygen sensor according to this invention.
Figure 1C:
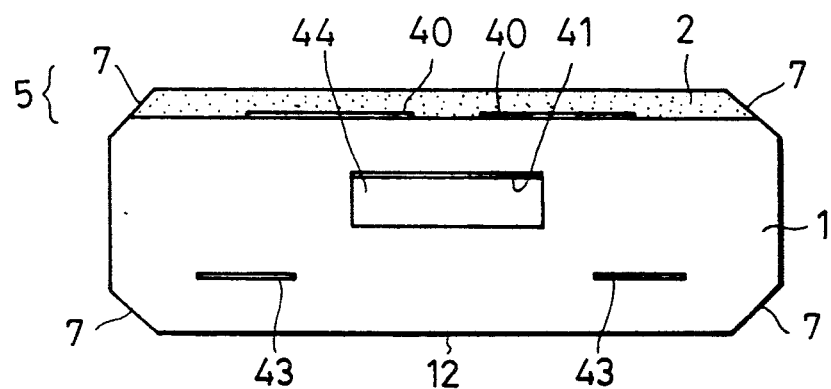
FIGS. 1(c) and 1(d) are respective cross-sectional views taken on the plane of the line I—I of FIG. 1(b)

As shown in FIGS. 1(b), (c), and (d), chamfers 7 are formed by chamfering four ridges of the section, which is the extending part of the oxygen sensor element 12 from a ceramic supporter 28a and is exposed to exhaust gas, the edges being parallel to the lengthwise direction of the oxygen sensor element 12.

Forming these chamfers 7 at the two edges consisting of the porous protective layer 2 is the most effective way to decrease thermal stress from the temperature difference between the inside and the outside of the oxygen sensor element 12.

Although chamfering is applied to the four edges in a cross section of a solid electrolytic body and a porous protective layer as shown in FIGS. 1(b), (c), and (d), chamfering applied to only the two edges consisting of the porous protective layer is sufficiently effective in releasing thermal stress from the oxygen sensor element.

Figure 1D:
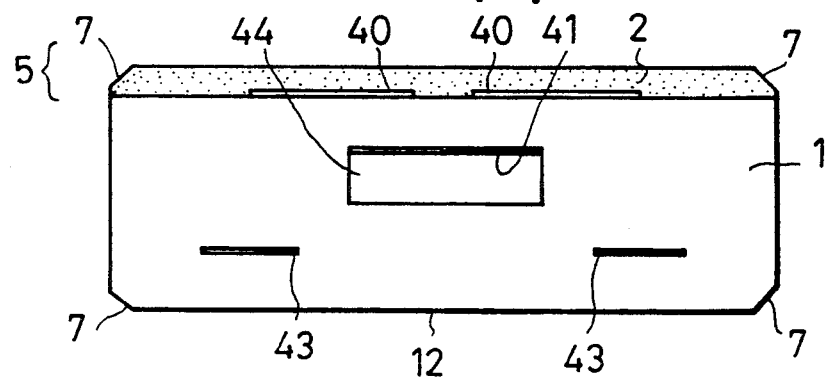

It is, as shown in FIG. 1(c), most effective in releasing thermal stress from the oxygen sensor element to apply chamfering to the two edges consisting of a porous protective layer 2 to give chamfers exposing both the porous protective layer 2 and the solid electrolytic body 1. However, it releases sufficient thermal stress from the oxygen sensor element to apply chamfering to the two edges consisting of a porous protective layer 2 to give chamfers exposing only the porous protective layer 2, as illustrated in FIG. 1(d).

This plate oxygen sensor element 12 is fixed and sealed to a cylindrical metal cap 10 through talc (30a and 30b) which fills space between ceramic supporters 28a, 28b and 28c. Such fixing of the oxygen sensor element 12 is carried out by compressing talc powder 30a and 30b through ceramic supporters 28a, 28b and 28c.

At the opposite side of the cap 10 to the side which is fixed to a housing 4 through an airtight ring 11, a rubber stopper 14 with a lead wire 13 inserted is caulked with the cap 10 and makes the cap 10 airtight. The end of the lead wire 13 is electrically connected to a terminal electrode of the oxygen sensor element 12. Numeral 3 denotes a protective cover.

In the oxygen sensor 20 thus constructed, even when thermal stress created from exhaust gas and/or the built-in heaters is caused at the section of the oxygen sensor element 12 to be exposed to the exhaust gas, stress concentration is not created and oxygen concentration detecting function is not damaged.

FIG. 2 shows the results of the examination of the crack occurrence when a conventional oxygen sensor and the oxygen sensor of this invention were subjected to thermal shock test.

The thermal shock test was conducted in the following manner:

the heater built in the oxygen sensor element was provided with electrical power to heat the oxygen detection section for 60 seconds (the temperature of the oxygen detection section was regulated by varying the electrical power supply), and air was blown on the oxygen sensor element at the rate of 10 m/sec for 60 seconds at room temperature (10° to 20° C.), then the rate of crack occurrence was examined after 10 cycles of the heating and blowing.

FIG. 2 shows that crack occurrence from thermal stress could be sufficiently prevented by applying chamfering to the oxygen sensor element in the present invention.

Figure 3A:
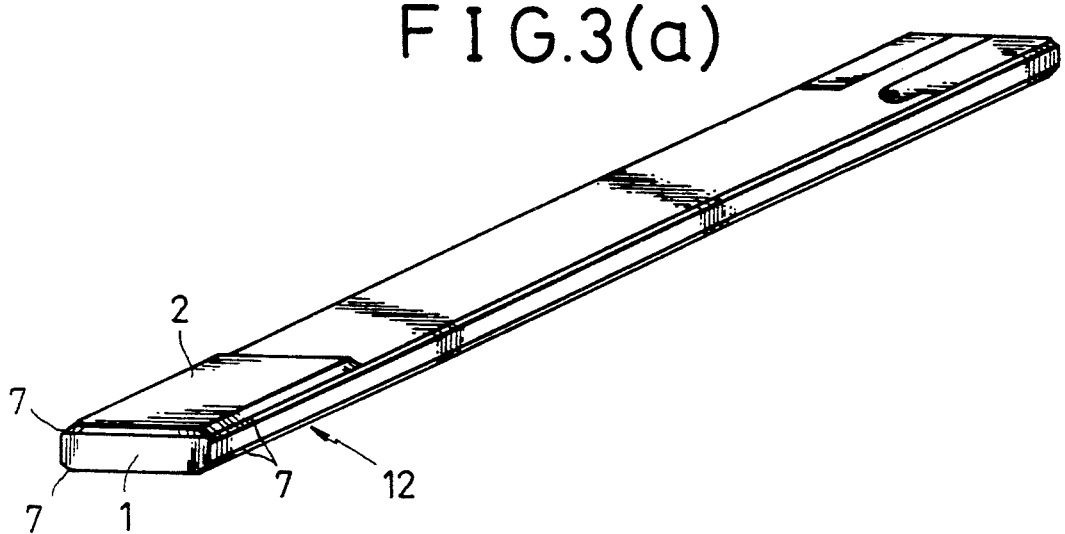
FIGS. 3(a) to 3(d) are respective perspective views illustrating other examples of the oxygen sensor element in the present invention.
Figure 3B:
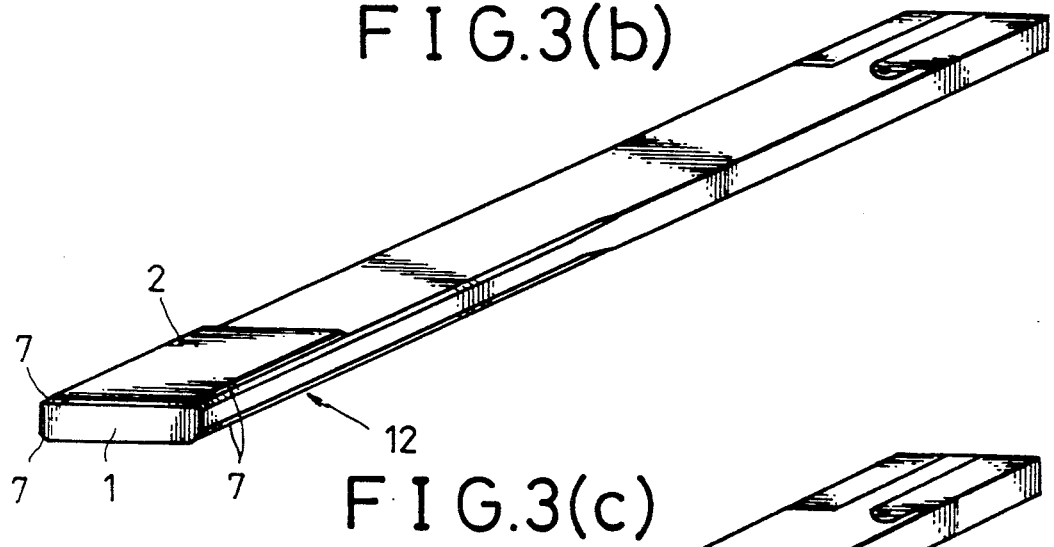
Figure 3C:
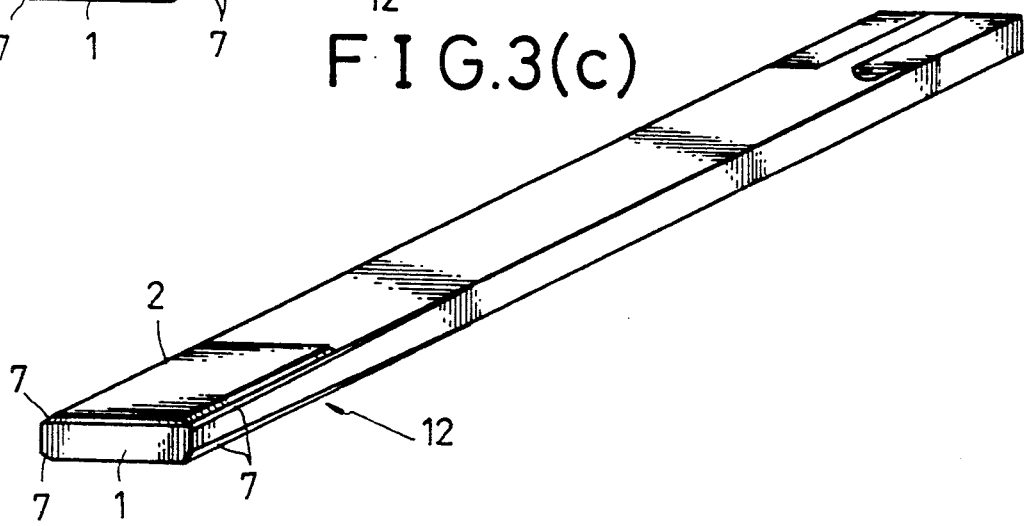
Figure 3D:
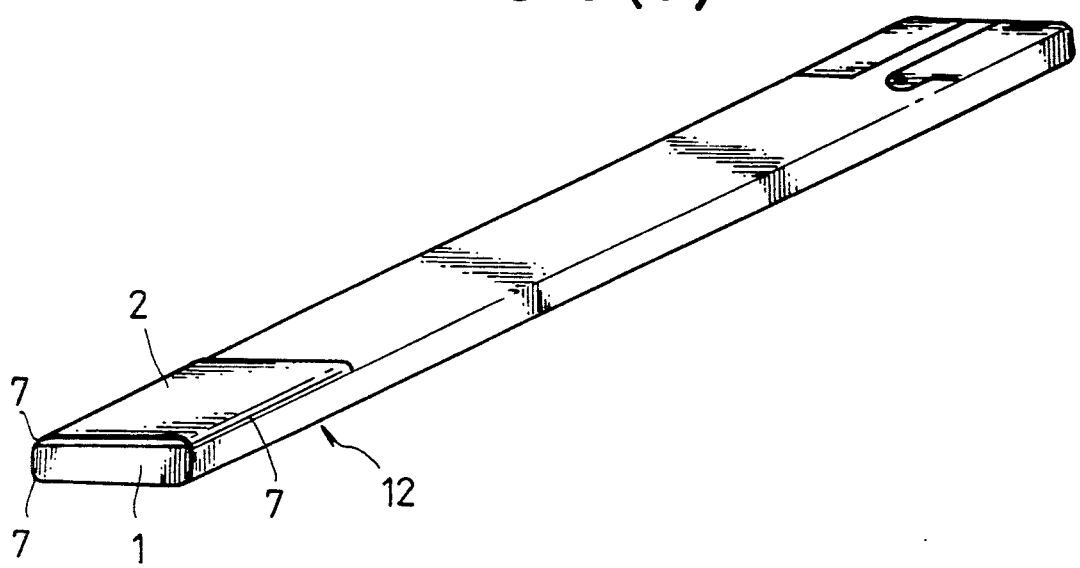
Figure 4:
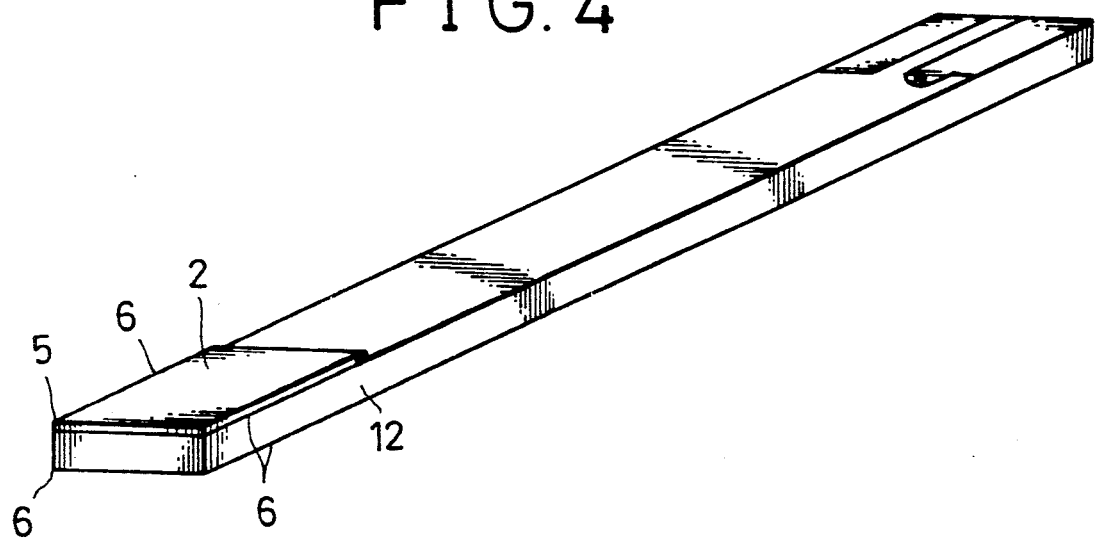
FIG. 4 is a perspective view illustrating a conventional oxygen sensor element.

Although the invention has been described in connection with preferred embodiments, changes and modifications may be made within the scope of the appended claims. Although, in the above-mentioned embodiments, chamfering was applied only to the extending section of the oxygen sensor element from the ceramic supporter 28a, entire edges may be chamfered as shown in FIG. 3(a). Also, chamfering is allowed to be applied to the halfway of the edges, as shown in FIG. 3(b). Furthermore, the edges may be chamfered in a taper-shape or R-shape, shown in FIG. 3(c) and FIG. 3(d), respectively.

In the above embodiments, all the four edges are chamfered; however, as described before, only the two edges consisting of the porous protective layer may be chamfered depending upon the thermal stress applied to the oxygen sensor element in use. It is needless to say that chamfering may be applied not only to the edges formed parallel to the lengthwise direction of the oxygen sensor element but also to the edges formed perpendicular to the lengthwise direction of the oxygen sensor element.

Even if the oxygen sensor element has no built-in heater, the oxygen sensor can have extremely high durability against thermal impulses such as rapid temperature change of exhaust gas from internal combustion engine and the like.

As has been explained, according to the oxygen sensor of this invention, since chamfering is applied to the edges of the oxygen sensor element, cracks do not occur; therefore, oxygen concentration detecting function is not damaged even when the oxygen sensor element is thermally stressed, so that an oxygen sensor which has resistance to thermal stress can be obtained.

What is claimed is:

1. An oxygen sensor comprising
an oxygen sensor element in the form of an elongated plate having an oxygen detection section having defined edges at the end of said oxygen sensor element, said oxygen detection section generating electromotive force between electrodes according to oxygen concentration or varying electrical resistance, said oxygen detection section generating electromotive force comprising a measuring electrode formed on one surface of a solid electrolytic body, a porous protective layer, and a reference electrode formed on the other surface of the solid electrolytic body, chamfering being applied to edges formed parallel to the lengthwise direction of said oxygen sensor element which is exposed to gas to be measured.

2. An oxygen sensor according to claim 1, wherein chamfering is applied to both the porous protective layer and the solid electrolytic body.

3. An oxygen sensor according to claim 1, wherein the edges are chamfered in a taper-shape.

4. An oxygen sensor according to claim 1, wherein the edges are chamfered in R-shape.

* * * * *